United States Patent [19]
Wong

[11] Patent Number: 5,341,214
[45] Date of Patent: * Aug. 23, 1994

[54] NDIR GAS ANALYSIS USING SPECTRAL RATIOING TECHNIQUE

[75] Inventor: Jacob Y. Wong, Santa Barbara, Calif.

[73] Assignee: Gaztech International Corporation, Goleta, Calif.

[*] Notice: The portion of the term of this patent subsequent to Nov. 17, 2009 has been disclaimed.

[21] Appl. No.: 851,869

[22] Filed: Mar. 16, 1992

Related U.S. Application Data

[63] Continuation-in-part of Ser. No. 793,990, Nov. 18, 1991, Pat. No. 5,163,332, which is a continuation of Ser. No. 604,615, Oct. 26, 1990, abandoned, which is a continuation-in-part of Ser. No. 503,216, Apr. 2, 1990, Pat. No. 5,060,508, and a continuation-in-part of Ser. No. 503,215, Apr. 2, 1990, Pat. No. 5,103,096, which is a continuation-in-part of Ser. No. 403,587, Sep. 6, 1989, Pat. No. 5,026,992.

[51] Int. Cl.$^5$ .............................................. G01N 21/03
[52] U.S. Cl. ................................. 356/437; 356/440; 250/343
[58] Field of Search ..................... 356/437, 440, 435; 250/573, 576, 343

[56] References Cited

U.S. PATENT DOCUMENTS

| | | | |
|---|---|---|---|
| 3,860,818 | 1/1975 | Stalder et al. | 356/437 |
| 3,935,463 | 1/1976 | Jacobsen | 356/439 |
| 4,673,812 | 6/1987 | Yoneda | 250/343 |
| 5,125,742 | 6/1992 | Wilks | 356/440 |
| 5,163,332 | 11/1992 | Wong | 356/437 |

Primary Examiner—Richard A. Rosenberger
Attorney, Agent, or Firm—Daniel C. McKown

[57] ABSTRACT

An instrument for determining the concentration of a particular gas that might be present in a sample has no moving parts and is extremely compact and inexpensive. A novel waveguiding structure serves both as an optical element and as the sample chamber. As an optical element, the waveguiding structure collects radiation from a blackbody source located at the entrance end of the waveguiding structure and conducts the radiation through the waveguiding structure, concentrating it on two infrared detectors mounted at the opposite end of the waveguiding structure. As a sample chamber, the waveguiding structure causes the radiation to undergo multiple reflections that result in the average path length being substantially greater than the physical length of the waveguiding structure. Each of the detectors has its own optical filter, and baffling assures that each detector responds only to radiation which has passed through its filter. One filter defines a spectral passband that coincides with the infrared absorption band of the gas to be measured. The other filter defines a non-absorbing or neutral passband. The electrical signals produced by the detectors are processed to provide a ratio, the value of which is related to the concentration of the particular gas to be detected.

9 Claims, 2 Drawing Sheets

NDIR GAS ANALYSIS USING SPECTRAL RATIOING TECHNIQUE

REFERENCE TO RELATED APPLICATIONS

The present application is a continuation-in-part of U.S. patent application Ser. No. 07/793,990 filed Nov. 18, 1991 for "Improved Gas Sample Chamber," now U.S. Pat. No. 5,163,332, which was a continuation of U.S. patent application Ser. No. 07/604,615 filed Oct. 26, 1990, now abandoned which was a continuation-in-part of U.S. patent application Ser. No. 07/503,216 filed Apr. 2, 1990 and issued Oct. 29, 1991 as U.S. Pat. No. 5,060,508. The present application is also a continuation-in-part of U.S. patent application Ser. No. 07/503,215 filed Apr. 2, 1990 for "Rapid Fire Detector," now U.S. Pat. No. 5,103,096, which was a continuation-in-part of U.S. patent application Ser. No. 07/403,587 filed Sep. 6, 1989, which issued as U.S. Pat. No. 5,026,992 on Jun. 25, 1991.

BACKGROUND OF THE INVENTION

1. Field of the Invention

The present invention is in the field of non-dispersive infrared (NDIR) gas analyzers of a type typically used to measure the concentration of an undesirable gas so that an alarm can be given when its concentration approaches a preset level. The present invention achieves this result in a simple and elegant manner without the use of moving parts. Typically, such gas analyzers could be used as the basis for fire detectors and ventilation controllers, as well as detectors of toxic or explosive gases.

2. The Prior Art

The NDIR technique utilizes the characteristic infrared absorption bands of gases for the detection of these gases. The term "non-dispersive" as used herein refers to the apparatus used, typically a narrow-band optical or infrared transmission filter instead of a dispersive element such as a prism for isolating for purposes of measurement the radiation in a particular wavelength band that normally coincides with a strong absorption band in the absorption spectrum of a gas to be measured.

One of the earlier NDIR gas analyzers is described in U.S. Pat. No. 3,793,525 to Burch, et al. In their invention, a beam of infrared energy emanates from an infrared source and passes through a sample chamber containing an unknown gas mixture. Before reaching an infrared detector, the beam is passed through one or more narrow bandpass filters, which may be mounted on a filter wheel. Typically, each filter passes only radiation at the characteristic absorption wavelength of a particular gas of interest. Another filter may also be used as a reference channel at a wavelength that does not overlap the characteristic absorption wavelength of any of the gases present in the sample cell. The use of a rotating filter wheel is typical of the earlier gas analyzers.

In U.S. Pat. No. 3,811,776, Blau, Jr. describes another of the early NDIR gas analyzers. His analyzer exemplifies a class of instruments that use, in addition to the gas sample chamber, a reference sample chamber containing the gas of interest and an identical sample chamber evacuated or filled with a gas that is transparent at the wavelength of the absorption band of the gas to be measured. These additional two chambers are alternately moved into and out of the radiation beam. Since the sample chamber is placed in series with these cells, the alternate introduction of the absorbing and non-absorbing cells into the radiation beam creates, respectively, a reference detector signal and a sample detector signal whose ratio is used to determine the gas concentration in the sample chamber. Unlike the invention of Burch, et al. which utilizes two interposed optical filters to create a sample signal and a reference detector signal, the Blau, Jr. configuration takes advantage of the principle of nonlinear absorption by the gas to be measured (as discussed in U.S. Pat. No. 4,578,762 of Wong), in order to create the reference and sample signals.

In U.S. Pat. No. 4,499,379, Miyatake, et al. and in U.S. Pat. No. 4,501,968, Ebi, et al. show a gas analyzer having a sample cell the interior surface of which is a mirror surface. The gas to be analyzed is heated within the sample cell and the entire volume of gas serves as the source of radiation. Thus, the mirror surface on the inside of the sample cell does not appear to be used in bringing the radiation to bear on the detectors. Two detectors are used, and each has its own filter. The radiation is chopped by means of a rotating mechanical chopper.

These earlier NDIR gas analyzers found acceptance as laboratory instruments in a number of fields, but there remained a need for reducing the size and complexity of the instruments.

The next step in that direction was taken by Wong in U.S. Pat. No. 4,694,173. He proposed NDIR techniques that did not require moving parts, such as mechanical choppers. The goal was to render sensors more rugged and compact for use in a host of new applications.

In U.S. Pat. No. 4,567,366 filed Sep. 26, 1983, Shinohara describes a methane sensor that uses a ratio technique, but the sample chamber is quite different from that of the present invention. The sample chamber is composed of a porous sintered metal or a plastic foam, and therefore is not capable of acquiring a mirror-like finish. In U.S. Pat. No. 4,709,150 filed Mar. 18, 1986, Burough, et al. also show a sample chamber that is composed of a porous plastic or a porous sintered metal.

A major step forward in devising a gas analyzer that is extremely compact and has no moving parts is described in U.S. Pat. No. 5,026,992 to Wong. His approach is to use a black body radiation source whose temperature is alternated between two temperatures such as 523 degree K and 723 degree K, typically, at a frequency on the order of 1 Hz. A single filter having two narrow passbands is used along with a single detector. In contrast, Shinohara uses a source having a constant output spectrum. In Shinohara's instrument, the calculated ratio is the ratio of the detected intensity at the absorption band of the gas to be detected to the intensity of the radiation at a different, reference, wavelength. In contrast, in Wong's technique, the calculated ratio is the ratio of the combined intensity at the absorption band and the reference band when the source is at a first temperature to the combined intensity of the two wavelength bands when the source is at a second temperature. The use of the dual temperature source eliminated the need for moving parts such as a mechanical chopper, thereby eliminating the bulky chopper wheel and its heavy electric motor.

A second major step toward reducing the size and cost of gas analyzers is described in U.S. Pat. No. 5,060,508, also to the present inventor, Wong. Wong discovered that by making the gas sample chamber in the form of a tube having a specularly-reflecting inner surface, the radiation introduced at one end of the tube is conducted with high efficiency to a detector at the other end of the tube and that the actual pathlength travelled by the radiation is substantially greater than the physical length of the tube because of the multiple reflections that occur within the tube. The use of this type of sample chamber considerably reduces the physical size of the gas analyzer.

In the present application, the present inventor describes an NDIR gas analyzer that combines a spectral ratioing technique with a light pipe gas sample chamber to achieve an instrument that is compact, inexpensive, and has no moving parts.

SUMMARY OF THE INVENTION

A major objective of the present invention is to provide a NDIR gas analyzer that has no moving parts and that is extremely compact and inexpensive. In the preferred embodiment, the instrument is easily held within one hand and costs approximately $20 to manufacture.

In accordance with the present invention, the gas sample chamber consists of a tube that has been polished to a mirror-like finish so as to conduct the radiation down the tube by multiple reflections. Because of the multiple reflections, the actual optical pathlength is substantially greater than the length of the tube.

Further in accordance with the present invention, a first filter having a narrow passband that includes an absorption band of the gas to be detected is positioned at the opposite end of the tube from the source. A second filter is positioned adjacent the first filter, and the second filter transmits only radiation in a spectral band that is not absorbed by the gas to be detected nor by any other commonly encountered gases in the atmosphere. A first detector receives only radiation that is passed through the first filter, and a second detector receives only radiation that is passed through the second filter. Cross-talk is prevented by a baffle that prevents radiation that has passed through the first filter from reaching the second detector and that prevents radiation that has passed through the second filter from reaching the first detector. Cross-talk can also be avoided by using the first and second filters respectively as the windows of the first and second detector canisters.

Further in accordance with the present invention, the tubular sample chamber includes at least one aperture in the wall of the tube, and this aperture is completely covered by a membrane that permits the gas to be detected to enter the tubular sample chamber by diffusion. The pore size of the membrane is so small that larger undesirable particles such as dust, smoke particles, and water droplets are prevented from entering the sample chamber.

In a preferred embodiment of the present invention, the electrical signals produced by the first and second detectors are applied to an electronic circuit that produces a signal that is representative of the ratio of the signals from the first detector and the second detector.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
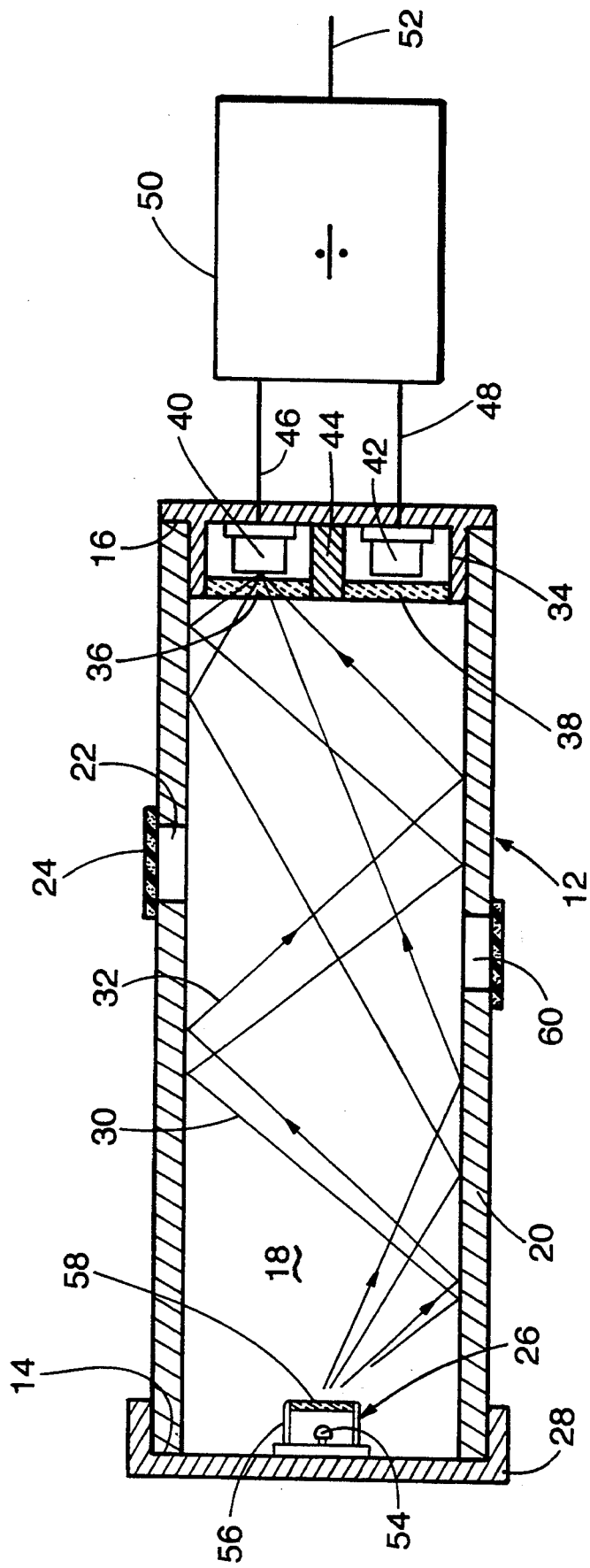
FIG. 1 is a diagrammatic side elevational view in cross section showing the gas sample chamber and related parts in a preferred embodiment of the invention; and, FIG. 2 is a diagrammatic side elevational view in cross section showing the gas sample chamber and related parts in an alternative embodiment of the invention.

In the preferred embodiment, the sample chamber of the gas analyzer takes the form of a tube 12 having a first end 14 and a second end 16. The inside surface 18 of the tube is polished to a mirror-like smoothness so that it is specularly reflective. The word specular as used here is derived from the Latin word speculum, meaning mirror. In one embodiment of the invention, the highly polished inside surface 18 of the tube 12 is coated with a very thin layer of a material that is highly reflective at the wavelength used. In the preferred embodiment, the tube 12 is composed of a metal, but in an alternative embodiment it is composed a plastic. The wall 20 of the tube 12 is non-porous, but it is provided with at least one aperture of which the aperture 22 is typical. The aperture 22 is covered by a membrane 24 through which the gas to be detected enters and leaves the sample chamber by diffusion. The membrane 24 prevents particles larger than approximately 0.01 micron from entering the sample chamber.

In the preferred embodiment, a source 26 is mounted in an end cap 28 that serves the dual purpose of closing the first end 14 of the tube 12 and of supporting the source 26. In the preferred embodiment, the source is a small incandescent lamp 54 in a housing 56 equipped with an IR transmitting window 58 such as silicon or sapphine. When an electric current is passed through the source, the source generates radiation, and in the preferred embodiment the radiation has spectral characteristics approaching those of an ideal blackbody. The source 26 radiates in every direction, and the typical rays 30 and 32 show that the radiation progresses along the tube 12 by multiple reflections.

At any particular time, the tube 12 contains air and it may also contain a particular gas that is to be detected, that has diffused into the tube 12 through the membrane 24.

It is important to note that in accordance with the present invention the gas to be detected must also be free to diffuse out of the sample chamber through, e.g., opening 60. Otherwise, the gas to be detected will stagnate within the sample chamber rendering the analyzer blind to further changes in the concentration of the gas to be detected.

In the preferred embodiment, the second end 16 of the tube 12 is closed by a housing 34 in which are mounted a first filter 36, a second filter 38, a first detector 40 and a second detector 42. In the preferred embodiment, a baffle 44 is interposed between the first filter 36 and the second filter 38, and between the first detector 40 and the second detector 42. The purpose of this baffle is to prevent radiation that has passed through the first filter 36 from entering the second detector 42 and to prevent radiation that has passed through the second filter 38 from entering the first detector 40. This eliminates "cross-talk" between the first and second channels.

Figure 2:
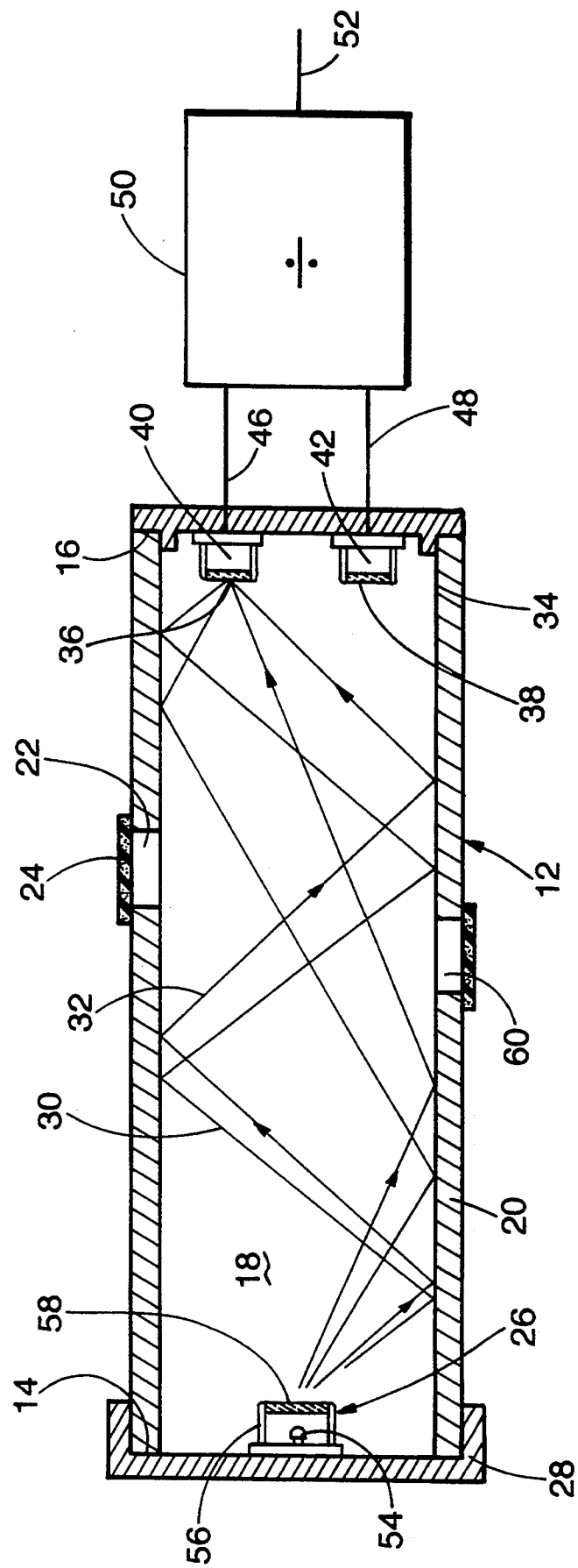

In another embodiment shown in FIG. 2, the filters 36 and 38 are respectively employed as windows for the canisters of detectors 40 and 42. In this embodiment no separate baffle is needed to avoid "cross-talk" between the first and second channels.

This elimination of cross-talk is a teaching that is opposite to the teaching in the present inventor's U.S. Pat. No. 5,026,992, in which radiation in two distinct wavelength bands falls simultaneously on a single detector, thereby intentionally producing maximum cross-talk.

In the preferred embodiment, the first filter 36 has a single narrow pass band that includes only the characteristic absorption wavelength band of the particular gas to be detected. The second filter 38 has a single narrow passband that does not include the characteristic absorption wavelength band of the particular gas, nor does it include an absorption band of any of the common gases of which the ambient air is composed. Thus, any variations in the output of the second detector cannot be caused by variations in the concentration of any of the gases present in the sample chamber 12, but instead must be caused by factors that affect both channels to the same extent. Examples of such factors include variations in the intensity of the source 26, variations in the power supply, and long-term degradation of the optical qualities of the tube 12. Since these factors affect both of the channels equally, the ratio of one channel to the other should be independent of these factors, and affected only by variations in the concentration of the particular gas to be detected.

The first detector 40 and the second detector 42 produce signals on the lines 46 and 48 respectively that are representative of the amount of radiation falling on the respective detectors. These signals are applied to an electronic circuit 50 that produces on the line 52 an output signal that in the preferred embodiment is representative of the ratio of the signal produced by the second detector to the signal produced by the first detector. Since the signal produced by the first detector decreases as the concentration of the particular gas increases, the ratio will increase as the concentration increases. As mentioned above, if the concentration of the particular gas is zero, the ratio should equal a constant, and if the channels are properly balanced, the constant will equal unity. In the preferred embodiment, the channels can be balanced initially by altering the gain in one of the channels until the quotient equals unity in the absence of the particular gas to be detected.

In an alternative embodiment, the electronic circuit produces a signal that is representative of the ratio of the signal from the first detector to the signal produced by the second detector. In this alternative embodiment, the signal produced by the electronic circuit decreases as the concentration of the particular gas increases.

Although it is possible for the analyzer to operate in a DC mode in which the source 26 emits a constant flow of radiation, in the preferred embodiment, the source 26 is pulsed at a low frequency (e.g., a few Hz), and synchronous detection of the pulsed signals on the lines 46 and 48 is employed. Electronic circuits such as the circuit 50 are considered routine in the art, and need no further elaboration. Likewise, it is apparent that the output signal on the line 52 from the electronic circuit 50 can be employed in a number of ways; for example, the signal could be used as the input to a servomechanism used for controlling a process or a machine, or alternatively, the signal could be applied to a threshold circuit for producing an alarm when the concentration of the particular gas exceeds a preset level.

Thus, there has been described an extremely simple and compact gas analyzer that has no moving parts when in operation and that is extremely inexpensive.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. An instrument for determining the concentration of a particular gas that might be present in the air around the instrument based on the propensity of the particular gas to absorb radiation in a characteristic wavelength band in which air not containing the particular gas does not absorb radiation, said instrument comprising in combination:

a tube having an open first end, having an open second end, having an inside surface that is specularly reflective for conducting radiation along said tube by multiple reflections, having a wall, and having at least one aperture extending through the wall;

a membrane spanning said at least one aperture and permitting the particular gas to diffuse into said tube from the air around the instrument and out of said tube, while preventing unwanted particles from entering said tube;

a source of radiation located within the first end of said tube;

a first filter located within the second end of said tube and oriented to receive radiation that has passed through said tube, and transmitting only radiation in a spectral band that includes the characteristic wavelength band of the particular gas;

a first detector located within the second end of said tube and positioned to receive only radiation that has passed through said first filter and responsive to that radiation to produce a first electrical signal representative of the intensity of that radiation;

a second filter located within the second end of said tube and oriented to receive radiation that has passed through said tube, and transmitting only radiation in a spectral band that does not include the characteristic wavelength band of the particular gas; and a second detector located within the second end of said tube and positioned to receive only radiation that has passed through said second filter and responsive to that radiation to produce a second electrical signal representative of the intensity of that radiation.

2. The instrument of claim 1 further comprising a baffle interposed between said first filter and said second filter, and between said first detector and said second detector, preventing radiation that has passed through said first filter from reaching said second detector and preventing radiation that has passed through said second filter from reaching said first detector.

3. The instrument of claim 2 further comprising a housing attached to the second end of said tube, supporting said first filter, said first detector, said second filter, and said second detector, said housing including said baffle.

4. The instrument of claim 1 wherein said source is an electrically-powered blackbody.

5. The instrument of claim 4 further comprising in combination means for electrically modulating the temperature of the electrically-powered blackbody at a low frequency.

6. The instrument of claim 1 further comprising in combination: electronic means electrically connected to said first detector and receiving the first electrical signal, and electrically connected to said second detector and receiving the second electrical signal, for producing a quotient signal representing the ratio of said second electrical signal to said first electrical signal.

7. The instrument of claim 1 further comprising in combination:
a first canister connected to the second end of said tube, having an aperture to admit radiation, containing said first detector, and supporting said first filter so that it spans the aperture of said first canister; and,
a second canister connected to the second end of said tube, having an aperture to admit radiation, containing said second detector, and supporting said second filter so that it spans the aperture of said second canister.

8. In a ratioing type of NDIR gas analyzer for use in determining the concentration of a particular gas that might be present in the air based on the propensity of the particular gas to absorb radiation in a characteristic wavelength band in which air not containing the particular gas does not absorb radiation, having a source of blackbody radiation, having a first filter that transmits only radiation in a spectral band that includes the characteristic wavelength band of the particular gas, having a first detector that receives only radiation that has passed through said first filter, having a second filter that transmits only radiation in a spectral band that does not include the characteristic wavelength band of the particular gas, and having a second detector that receives only radiation that has passed through said second filter, the improvement comprising:
a tube having an open first end in which said source is located, having an open second end, having an inside surface that is specularly reflective for conducting the radiation along said tube by multiple reflections, having a wall, and having at least one aperture extending through the wall;
a membrane spanning said at least one aperture and permitting the particular gas to diffuse into said tube from the air around the instrument while preventing unwanted particles from entering said tube; and,
a housing attached to the second end of said tube, supporting said first filter, said first detector, said second filter, and said second detector, said housing further including a baffle interposed between said first filter and said second filter, and between said first detector and said second detector, preventing radiation that has passed through said first filter from reaching said second detector and preventing radiation that has passed through said second filter from reaching said first detector.

9. In a ratioing type of NDIR gas analyzer for use in determining the concentration of a particular gas that might be present in the air based on the propensity of the particular gas to absorb radiation in a characteristic wavelength band in which air not containing the particular gas does not absorb radiation, having a source of blackbody radiation, having a first filter that transmits only radiation in a spectral band that includes the characteristic wavelength band of the particular gas, having a first detector that receives only radiation that has passed through said first filter, having a second filter that transmits only radiation in a spectral band that does not include the characteristic wavelength band of the particular gas, and having a second detector that receives only radiation that has passed through said second filter, the improvement comprising:
a tube having an open first end in which said source is located, having an open second end, having an inside surface that is specularly reflective for conducting the radiation along said tube by multiple reflections, having a wall, and having at least one aperture extending through the wall;
a membrane spanning said at least one aperture and permitting the particular gas to diffuse into said tube from the air around the instrument while preventing unwanted particles from entering said tube;
a first canister connected to the second end of said tube, having an aperture to admit radiation, containing said first detector, and supporting said first filter so that it spans the aperture of said first canister; and,
a second canister connected to the second end of said tube, having an aperture to admit radiation, containing said second detector, and supporting said second filter so that it spans the aperture of said second canister.

* * * * *